United States Patent
Persson (10) Patent No.: US 9,814,852 B2
(45) Date of Patent: Nov. 14, 2017

(54) TRACHEOSTOMA PLASTER

(75) Inventor: Jan-Ove Persson, Höör (SE)

(73) Assignee: Atos Medical AB (SE)

( * ) Notice: Subject to any disclaimer, the term of this patent is extended or adjusted under 35 U.S.C. 154(b) by 1231 days.

(21) Appl. No.: 13/140,575

(22) PCT Filed: Dec. 18, 2009

(86) PCT No.: PCT/EP2009/067500
§ 371 (c)(1),
(2), (4) Date: Jun. 17, 2011

(87) PCT Pub. No.: WO2010/070087
PCT Pub. Date: Jun. 24, 2010

(65) Prior Publication Data
US 2011/0247629 A1    Oct. 13, 2011

Related U.S. Application Data

(60) Provisional application No. 61/139,075, filed on Dec. 19, 2008.

(30) Foreign Application Priority Data

Dec. 19, 2008 (SE) ..................... 0802628

(51) Int. Cl.
*A61M 16/04* (2006.01)
*A61M 16/10* (2006.01)

(52) U.S. Cl.
CPC ....... *A61M 16/047* (2013.01); *A61M 16/0468* (2013.01); *A61M 16/1045* (2013.01)

(58) Field of Classification Search
CPC .............. A61M 16/08; A61M 16/0497; A61M 16/0488; A61M 16/06; A61M 16/04;
(Continued)

(56) References Cited

U.S. PATENT DOCUMENTS 2,786,469 A * 3/1957 Cohen ............... A61M 16/0465
128/200.26
3,334,631 A * 8/1967 Stebleton .......... A61M 16/0465
128/200.26
(Continued)

FOREIGN PATENT DOCUMENTS

CN    1662273 A    8/2005
DE    202004007566 U1    8/2004
(Continued)

OTHER PUBLICATIONS

International Serach Report for WO 2010/070087.
(Continued)

*Primary Examiner* — Kathryn E Ditmer
(74) *Attorney, Agent, or Firm* — Fishman Stewart PLLC (57) ABSTRACT

A device for holding a tracheostoma device over a tracheostoma of a patient including a passage having a distal and a proximal opening for receiving the tracheostoma device at the distal opening thereof. A flange may extend laterally, caudially, and cranially from the passage. The flange may have a proximal side facing the tracheostoma of the patient and a distal side facing outwardly from the patient. At least a part of said proximal side may include skin adhesive. The flange may have a higher moment of resistance in the caudal/cranial direction than in the lateral/medial direction for said device by having a higher moment of resistance in the caudal/cranial direction than in the lateral/medial direction for at least a part of said flange.

19 Claims, 6 Drawing Sheets

(58) Field of Classification Search
CPC ...... A61M 2016/0493; A61M 16/0465; A61M 16/047; A62B 9/04; A62B 18/086; B63C 11/02; A41D 13/1176
USPC ............ 128/202.27, 207.15, 207.17, 206.25, 128/207.14, 220.26; 602/43, 48; 600/120
See application file for complete search history.

(56) References Cited

U.S. PATENT DOCUMENTS

| | | | |
|---|---|---|---|
| 4,235,229 A * | 11/1980 | Ranford et al. ......... | 128/207.17 |
| 4,325,366 A | 4/1982 | Tabor | |
| 4,459,984 A * | 7/1984 | Liegner .................. | A61F 2/203 |
| | | | 128/207.15 |
| 4,592,750 A * | 6/1986 | Kay ...................... | A61F 5/4404 |
| | | | 604/277 |
| 5,042,468 A | 8/1991 | Lambert | |
| 5,054,482 A * | 10/1991 | Bales ................. | A61M 16/0465 |
| | | | 128/207.14 |
| 5,738,095 A | 4/1998 | Persson | |
| 5,749,360 A * | 5/1998 | Lacey et al. ............. | 128/207.14 |
| 5,819,734 A | 10/1998 | Deily et al. | |
| 6,135,111 A * | 10/2000 | Mongeon .............. | A61M 16/04 |
| | | | 128/200.21 |
| D516,212 S * | 2/2006 | Persson ........................ | D24/128 |
| 7,025,784 B1 | 4/2006 | Blom et al. | |
| D533,660 S * | 12/2006 | Persson ........................ | D24/128 |
| 8,684,983 B2 * | 4/2014 | Andersen ................. | A61F 5/445 |
| | | | 604/317 |
| 2005/0133028 A1 | 6/2005 | Pagan | |
| 2005/0166924 A1 * | 8/2005 | Thomas ................ | A61M 16/04 |
| | | | 128/207.14 |
| 2007/0255258 A1 * | 11/2007 | Matlock ............ | A61M 16/0465 |
| | | | 604/535 |
| 2009/0171153 A1 * | 7/2009 | Sutoh ................. | A61B 1/00154 |
| | | | 600/114 |
| 2010/0217215 A1 * | 8/2010 | Lykke et al. ................... | 604/344 |
| 2010/0258135 A1 * | 10/2010 | Persson ............... | A61M 16/047 |
| | | | 128/207.16 |
| 2013/0192604 A1 | 8/2013 | Persson et al. | |

FOREIGN PATENT DOCUMENTS

| | | |
|---|---|---|
| EP | 0396497 A1 | 11/1990 |
| WO | WO-2004/000401 A1 | 12/2003 |

OTHER PUBLICATIONS

English abstract for DE-202004007566.
English translation of Chinese Office Action for CN200980150978. 3, dated Jul. 1, 2013.

* cited by examiner

TRACHEOSTOMA PLASTER

CROSS-REFERENCES TO RELATED APPLICATION

This application claims priority to Sweden Patent Application 0802628-8 filed on Dec. 19, 2008, U.S. Provisional Application 61/139,075 filed on Dec. 19, 2008, and PCT/EP2009/067500 filed on Dec. 18, 2009, which are hereby incorporated by reference in their entireties.

TECHNICAL FIELD

This invention pertains in general to the field of a device for holding a tracheostoma device and a method for applying such a device. More particular the invention pertains to a device for holding a tracheostoma device over a tracheostoma of a patient, said device comprising a tubular portion, having a distal and a proximal opening, for receiving the tracheostoma device in the distal opening thereof; a flange, extending laterally, caudially, and cranially from the tubular portion at a proximal part of the tubular portion, said flange having a proximal side, intended to face the tracheostoma of the patient, and a distal side, intended to face outwardly from the patient, at least a part of said proximal side being skin adhesive.

BACKGROUND

A tracheostomy is a surgical procedure in which an opening is formed through the anterior surface of the neck into the trachea. The opening is referred to as a tracheostoma. A tracheostomy tube can be provided to extend between the tracheostoma and the trachea. A tracheostomy is performed for example when there is a malfunction, such as a result from injury or disorder, in respect of the nervous system or the respiratory passages, which malfunction results in an incapacity to obtain enough air. An inferior lung capacity or need of respiratory treatment may also result in a tracheostomy.

A laryngectomy is a surgical procedure, used for example to treat a carcinoma, which involves removal of the larynx or voice box and the creation of a tracheostoma. A consequence of the procedure is that the trachea is no longer connected to the pharynx but is diverted to the tracheostoma. After this procedure, normal nasal function is not possible. In a subject whose breathing functions normally, the nose and the mucous membrane lining of the nasal cavity perform important functions in conditioning inhaled air. The convoluted passages and rich blood supply serve to increase both the temperature and humidity of the inhaled air to minimise the differential in these parameters with those of the surface of the lungs. Normally some heat and moisture is also captured from exhaled air prior to its release to the atmosphere. The mucous lining of the nasal passages also serves to remove particulate matter, such as fine dust particles, pollutants and microorganisms, from the inhaled air, and the action of cilia transports mucous and any particles away from the lungs.

When a patient has received a laryngectomy, in effect all inhaled air enters the lungs via the tracheostoma, and the nose is effectively not involved in the inhalation process. Exhaled air may pass through the tracheostoma or, if a voice prosthesis has been fitted, the stoma can be occluded so that the exhaled air is diverted through the voice prosthesis into the pharynx and the mouth, enabling the patient to speak. It is desirable that the flow of the exhaled air be controlled by means of a tracheostoma valve. In these situations, the valve can be arranged to remain open during breathing but, with a small additional increase in exhaled air flow, can be closed to divert the airflow.

In this respect tracheostoma devices, such as filter devices, HME, breathing protectors, and speech valves, have been developed to enable moisturizing of inhaled air, removal of small particles and bacteriological substances in said inhaled air, and providing the patient with the ability to speech by closing the air passage through the tracheostoma by manual operation.

These tracheostoma devices are held in place by a tracheostoma device holder, arranged above the tracheostoma of the patient. The tracheostoma device holder is attached to the skin of the patient by a plaster, having an adhesive surface on the side of the plaster intended to be directed towards the patient in use. Either, the tracheostoma device holder is welded to the plaster, or the tracheostoma device holder is on an adhesive surface on the side of the plaster intended to be directed outwards from the patient in use.

U.S. Pat. No. 7,025,784 discloses a system wherein a circular tape, adhesive on both sides, is used to adhere a tracheostoma device holder, above the tracheostoma of the patient. However, this tape is accompanied by the drawbacks that the adhesive area towards the patient is limited by the area of the tracheostoma device holder. Otherwise, the tape will adhere to clothings etc. on the side facing outwardly from the patient. The user or applier will have to hold tubular part, while the skin adhesive part extends radially. Thus, it is difficult to adhere this system in pit in between the sternocleidomastoid muscles, at patients with sunken stomas, i.e. stomas that somewhat sunken into the throat of the patient, since the adhesive surface of the system inevitably will adhere to the walls of the pit before reaching the bottom of the pit with the central portion of the system. Sunken stomas are very frequent in the group of patients not having the two vertical sternocleidomastoid muscles on the neck cut during laryngectomy. Thus, this system is only suitable for mildly or non-sunken stomas. Furthermore, due to the stiffness needed to withstand flipping over at high speech pressure, the circular shape of the rigid portion prevents the system from allowing good accessibility with sunken stomas. Nevertheless, it is very common that these kind of systems still flip over, since the bad connection between adhesives and skin and the axial displacement of the speech pressure resulting in loosening of the system and need of unduly high speech pressure. Also, due to the types of tracheostoma device holders applied to these kinds of tapes are exclusively for multi usage. Thus, the tracheostoma device holder of this kind has to be cleaned with strong solvents in between usage. Also, in this way, guidance of the system during application to the patient is almost entirely absent, since the flexibility of the tape is too high. U.S. Pat. No. 4,325,366 and WO 2004/000401 disclose similar systems with planar and circular tape, and circular and convex tape, respectively.

In this respect U.S. Pat. No. 5,738,095 and U.S. Pat. No. 5,042,468 disclose systems wherein the tracheostoma device holder is welded to a plaster, to form planar and circular tracheostoma device holder/plaster systems. However, these systems are not suitable for patients with sunken stomas and are difficult to apply due to uniform plasticity of the systems. Thus, the tubular holding portion of the systems will be deformed during application, leading to a perhaps unsatisfactory holding action of the tracheostoma device.

Also, all of the tracheostoma device holder systems according to the prior art expose the entire adhesive surface on the side intended to face the patient, before application, whereby application is difficult due to high demands of exact and correct initial positioning of the tracheostoma device holder system is required. Otherwise, the tracheostoma device holder system has to be disengaged and repositioned.

Furthermore, in many hospitals the surgical steps during laryngectomy are adapted for creating stomas of substantially planar natures, to comply with the tracheostoma device holder system presently on the market. This adaptation includes the cutting of the two vertical sternocleidomastoid muscles on the neck.

Hence, an improved holder system for a tracheostoma device holder system would be advantageous, and in particular a tracheostoma device holder system allowing for convenient application of the system with improved positioning ability, improved resistance to deformation of the tracheostoma device holder, allowance for non-adhesive parts on the side facing outwardly from the patient, improved compliance with sunken stomas and even deeply sunken stomas, and improved compliance with manifoldness of stoma configurations.

SUMMARY

Accordingly, the present invention preferably seeks to mitigate, alleviate or eliminate one or more of the above-identified deficiencies in the art and disadvantages singly or in any combination and solves at least the above mentioned problems by providing a device for holding a tracheostoma device over a tracheostoma of a patient, said device comprising: a tubular portion, having a distal and a proximal opening, for receiving the tracheostoma device in the distal opening thereof; a flange, extending laterally, caudially, and cranially from the tubular portion at a proximal part of the tubular portion, said flange having a proximal side, intended to face the tracheostoma of the patient, and a distal side, intended to face outwardly from the patient, at least a part of said proximal side being skin adhesive, wherein a bracing means is arranged on the flange, extending in the caudal/cranial direction from the tubular portion.

Advantageous features of the invention are defined in the dependent claims.

BRIEF DESCRIPTION OF THE DRAWINGS

These and other aspects, features and advantages of which the invention is capable of will be apparent and elucidated from the following description of embodiments of the present invention, reference being made to the accompanying drawings, in which.

DETAILED DESCRIPTION

The following description focuses on an embodiment of the present invention applicable to a system for holding a tracheostoma device over a tracheostoma of a patient.

Figure 1:
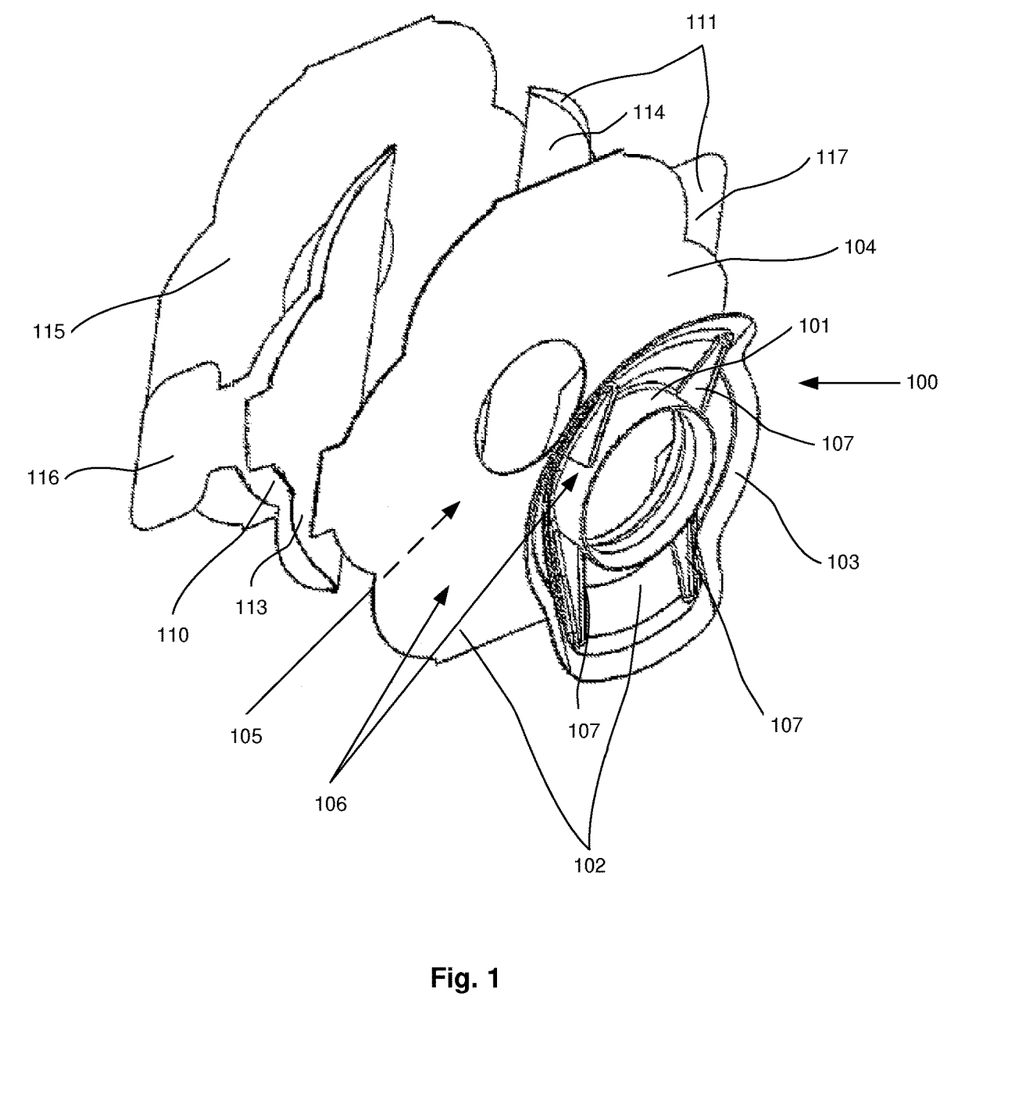
FIG. 1 is an exploded view of a device according to one embodiment of the present invention.

According to a first embodiment, disclosed as an exploded view in FIG. 1, a device 100 for holding a tracheostoma device, such as a HME, speech valve, etc, i.e. a tracheostoma device holder, is provided. The device comprises a tubular portion 101 for receiving the tracheostoma device in the distal end thereof. The tubular portion 101 may be of a circular cross-section, in a plane perpendicular to the central axis of the tubular portion 101. In the proximal end of the tubular portion 101 a flange 102 is provided, around the proximal opening of the tubular portion 101. The flange 102 comprises an inner rigid portion 103 and an outer more flexible portion 104. The flange 102 extends radially outwards from a proximal part of the tubular portion 101, in a plane perpendicular to the central axis of the tubular portion 101, said plane being the dorsal plane in use. The flange 102 has a proximal side 105, disclosed in a perspective view in FIG. 2, intended to face the tracheostoma of the patient, and a distal side 106, intended to face outwardly from the patient.

The tubular portion 101 may also be a tubular portion corresponding to the thickness of the flange 102, such as all 3-dimensional passages, creating a through hole, thus having a proximal and a distal opening.

The flange 102 is inclined, distally towards the central axis of the tubular portion 101, at least in the inner rigid portion 103. Preferably, the entire rigid portion 103 is inclined distally towards the central axis of the tubular portion 101, whereby improved contact with sunken stomas may be achieved.

Figure 3:
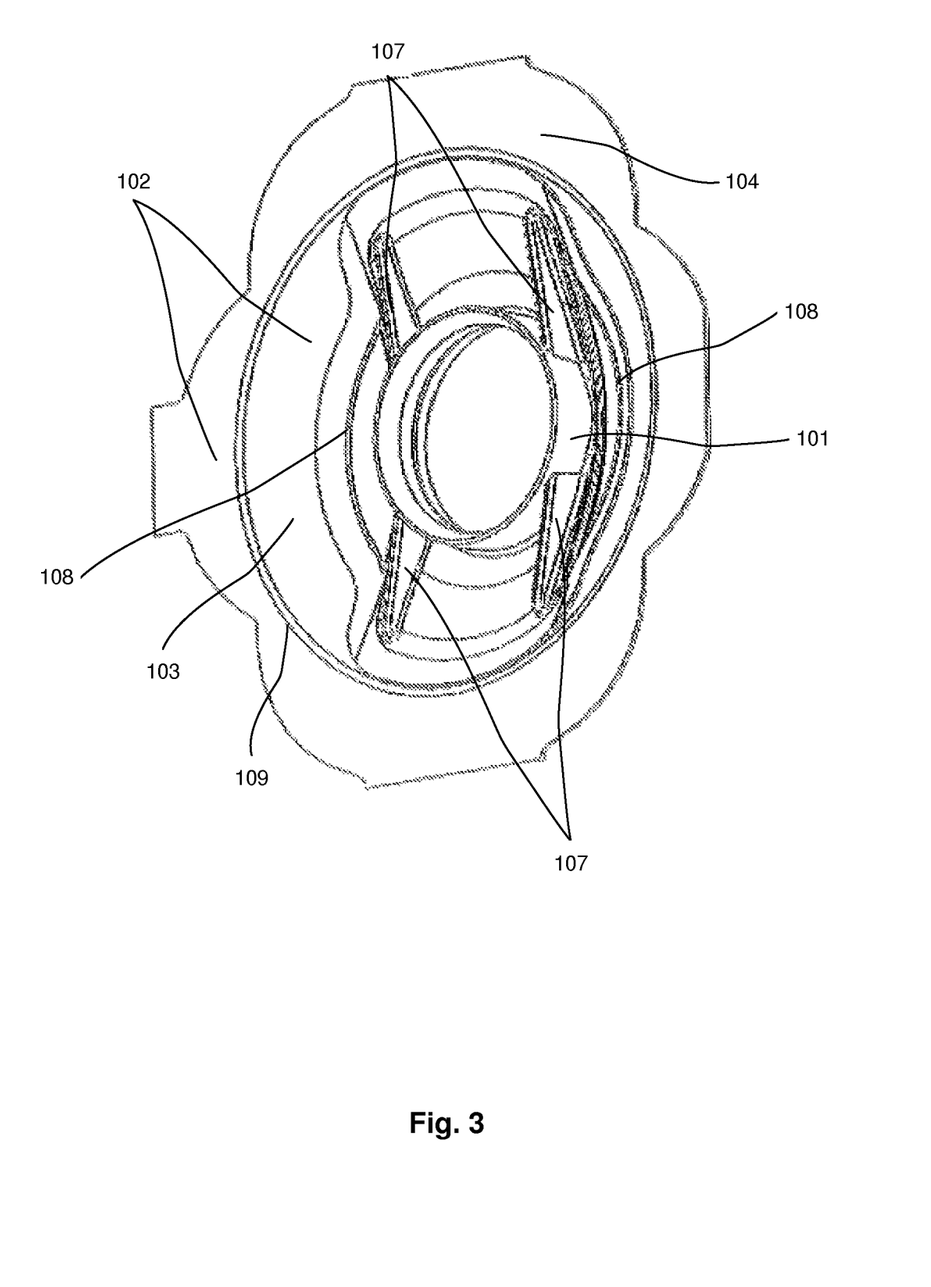
FIG. 3 is a perspective view of the distal side of a device according to one embodiment of the present invention.

The distal side of the flange 102, disclosed in a perspective view in FIG. 3, is provided with reinforcement. The reinforcement extends centrally in the caudal/cranial direction, giving a higher moment of resistance in the caudal/cranial direction than in the lateral/medial direction for the device 100. The higher moment of resistance in the caudal/cranial direction may be obtained by having a higher moment of resistance in the caudal/cranial direction than in the lateral/medial direction for at least a part of said flange 102. The reinforcement will absorb the speech pressure and transfer the obtained force centrally in the caudal/cranial direction. In this direction, there is more room for connection area between the device and the patient than in the lateral/medial direction, whereby flipping over may be prevented, while making the dimension in the lateral/medial direction smaller, allowing for improved accessibility with the entire depth of sunken stomas. The result will be improved resistance against flipping over, and better connection between the device and the stoma, leading to reduced risk of loosening of the device, evidently leading to undue leakage. The reinforcement may be a bracing means 107. Even if the bracing means 107 could be localized on the proximal side 105 of the flange 102, it is preferred to have the bracings 107 on the distal side 106, since such location would make possible a smooth and even contact surface between the device 100 and the skin of the patient. Also, it is convenient to have the bracings 107 on the distal side 106, since the inclination of the flange 102 allows for a concavely shaped distal side 106, whereby the bracings 107 may be placed confidently low, i.e. sufficiently far to the proximal end, to make possible a satisfactory stiffness, while simultaneously not being prone to interaction with clothing etc.

The bracing means 107 are preferably ribs extending in a plane perpendicular to the central axis of the tubular portion 101, thus being the dorsal plane in use. In this connection the ribs extend in the caudal/cranial direction. However, the bracing means 107 may also be a higher material thickness in the caudal/cranial direction than in the lateral/medial direction.

In one embodiment, two ribs extend substantially tangentially with the circular tubular portion 101 and parallel with each other, such that they in use extend along the caudal/cranial extension of the neck of the patient. In this way the device 100 may have a heterogeneous plasticity, whereby the device 100 has a higher deformation resistance in the direction parallel with the extension of the bracing means 107, i.e. the caudal/cranial direction, than in the direction perpendicular to the extension of the bracing means 107, i.e. the medial direction. Thus, the flange 102 of the device 100 may be compressed medially, i.e. in a direction perpendicular to the caudal/cranial direction, while keeping the shape of the tubular portion 101, thereby assuring that the positioning of the tubular portion 101 over the stoma and in between the two sternocleidomastoid muscles is achieved. Thus, no cutting of the two sternocleidomastoid muscles is necessary when using the device according to the present invention. Due to the convexly shaped proximal side of the flange 102, the device may come in good skin contact also on sunken stomas.

Along and adjacent the bracing means 107 in the caudal/cranial direction the device is provided with two weakening lines 108, to further increase the difference in moment of resistance between the caudal/cranial direction and the lateral/medial direction for said device 100. In this way the weakening lines 108 give rise to a reinforcement in the caudal/cranial direction.

Figure 2:
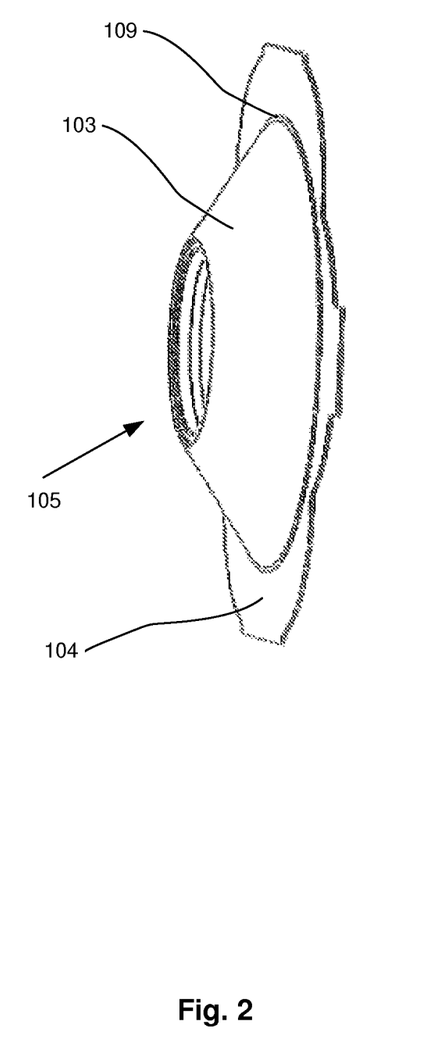
FIG. 2 is a perspective view of the proximal side of a device according to one embodiment of the present invention.

The proximal side 105 of the flange 102 is skin-adhesive. In one embodiment only parts of the proximal side 105 is skin-adhesive. The skin-adhesive part may extend all the way from the periphery of the device to the tubular portion 101. In this connection the skin adhesive part may be the proximal side of a flexible sheet onto which the more rigid inner part 103 is welded by a weld 109. Thereby, the outer part of the flexible sheet, skin-adhesive on the proximal side, will be the flexible part 104 of the flange 102. Preferably, the weld 109 is located radially distanced from the tubular portion 101, such as at the periphery of the more rigid part 103. In this way, the skin-adhesive part may be adhered to the skin at higher stress conditions in the distal direction, since the weld 109 will take up the stress on a distance away from the edge of the skin adhesive part.

The inner rigid portion 103 of the flange 102 is preferably oval, having its approximated longest diameter in the same direction as the extension direction of the bracing means 107, i.e. in the caudal/cranial direction of a caudal/cranial axis. Similarly, the approximated shortest diameter is in the lateral/medial direction of a lateral/medial axis. Also the outer more flexible portion 104 may be substantially circular or oval with indentations, such that for example a flower shape is obtained. In this way it may be easier to adhere the outer parts of the flange to the skin of the patient, without the need of folding the flexible portion to compensate for irregularities in the shape of the neck of the patient. In this way the contact area between the device 100 and the skin of the patient may be kept sufficiently high, within the two sternocleidomastoid muscles, to allow for safe attachment of the device to the skin of patients with sunken stomas.

On the proximal side 105 of the flange 102 a series of non-adhesive covering sheets may be arranged, for facilitating transportation, storing, and application of the device 100.

Figure 4:
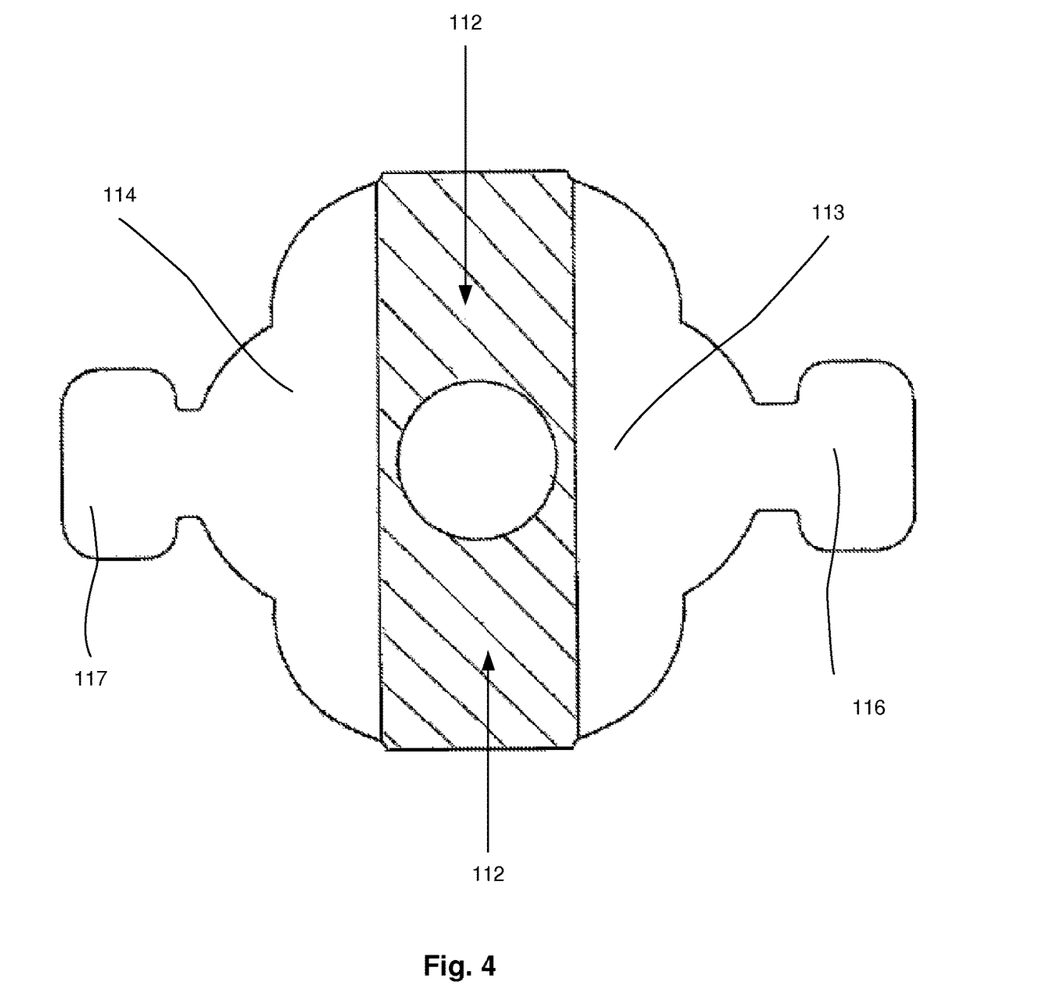
FIG. 4 is a side view from of the proximal side of a device according to one embodiment of the present invention, during a specific state.

In FIG. 4 a side view from the proximal side of device 100 is disclosed with a series of non-adhesive covering sheets. On top of the proximal, skin-adhesive surface 105, surrounding the proximal opening of the device 100, a first and a second covering sheet 110, 111 are applied. The first and the second covering sheet 110, 111 are applied from the tubular element 102 laterally on each side of the tubular element 102, respectively, covering side segments of the adhesive surface 105. Thus, a central/medial segment 112 of the adhesive surface 105 will still be uncovered by covering sheets 110, 111. The central/medial segment 112 of the adhesive surface will be the surface that in use will extend upwards and downwards from the tubular element 102 in a caudal/cranial direction, said central/medial segment 111 being adapted in size and form to fit within the two sternocleidomastoid muscles. The first and second covering sheets 110, 111 comprise folded parts 113, 114, respectively, that are folded laterally.

Figure 5:
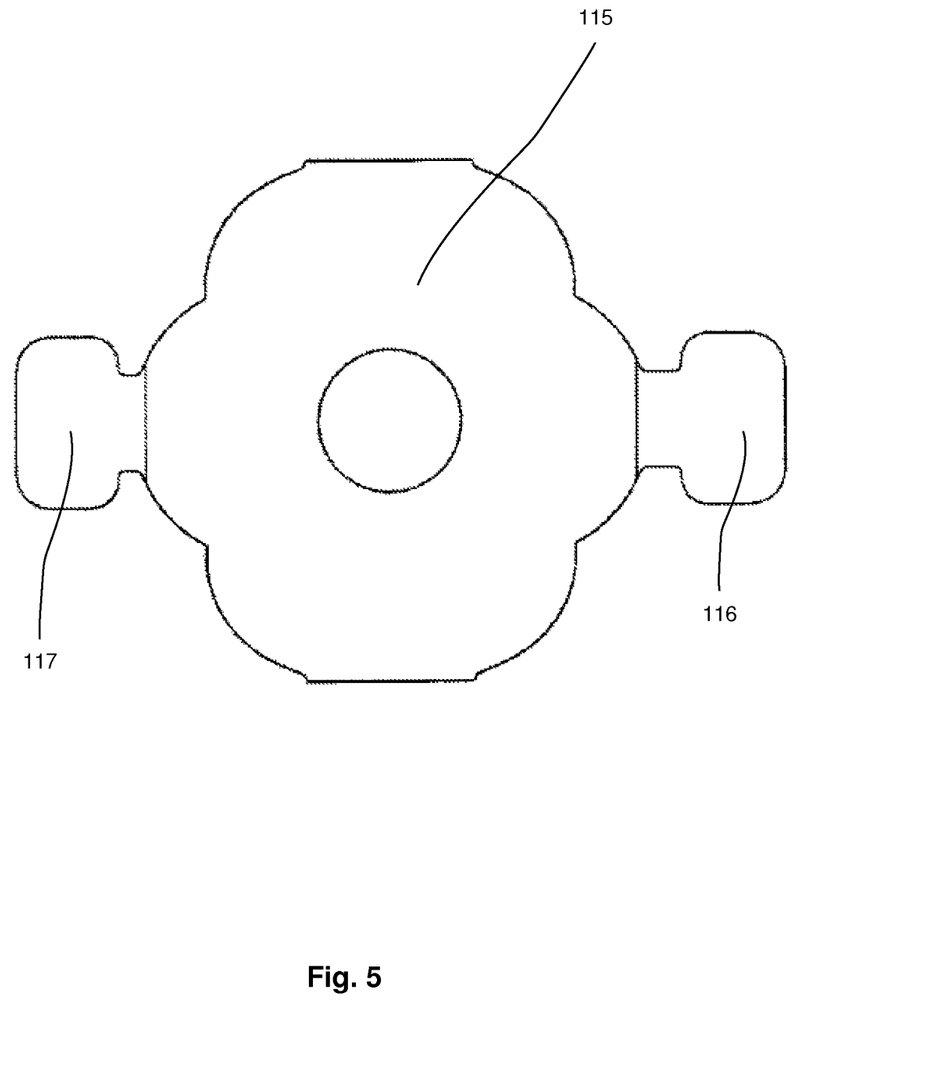
FIG. 5 is a side view from of the proximal side of a device according to one embodiment of the present invention, during a specific state.

A third covering sheet 115 is applied on top of the central/medial segment 112, as disclosed in FIG. 5, being a side view from of the proximal side of a device according to one embodiment of the present invention. In one embodiment the third covering sheet 115 covers at least partly the first and second covering sheets 110, 111, such that at least the edge between the first and second covering sheets 110, 111 and the central/medial segment 112 is covered. In this way the third covering sheet does not only finalize the covering of the adhesive surface on the proximal side of the flange 102, but also protects the edge between the first and second covering sheets 110, 111 from being unwillingly peeled off and thus uncovering the skin-adhesive surface of the flange 102, which of course is unwanted during transportation and storing.

In one embodiment still another covering sheet (not shown) may be applied. In this embodiment the third covering sheet 115 needs only to cover the central/medial/cranial part of the central/medial segment 112, while the still another covering sheet covers central/medial/caudal part of the central/medial segment 112.

To improve the covering ability of the covering sheets 110, 111, and 115 the covering sheets 110, 111, and 115 are heat shaped together with the device 100, to obtain the three-dimensional convex shape at the proximal surface of the device 100. Thus, it is preferred to manufacture the covering sheets 110, 111, and 115 in a polymer with low melting point, such as polyethylene, preferably covered by a silicone sheet for improved separation between the adhesive surface and the covering sheets.

The folded parts 113, 114 extend at least partly laterally of the periphery of the device 100, i.e. the periphery of the flange 102. In one embodiment the folded parts comprises one gripping flap 116, 117 each, said flaps 116, 117 extending beyond the periphery of the device 100, such that the flaps are accessible from the front after the device 100 has been positioned over the stoma. For easy access, the flaps 116, 117 extend laterally.

Figure 6:
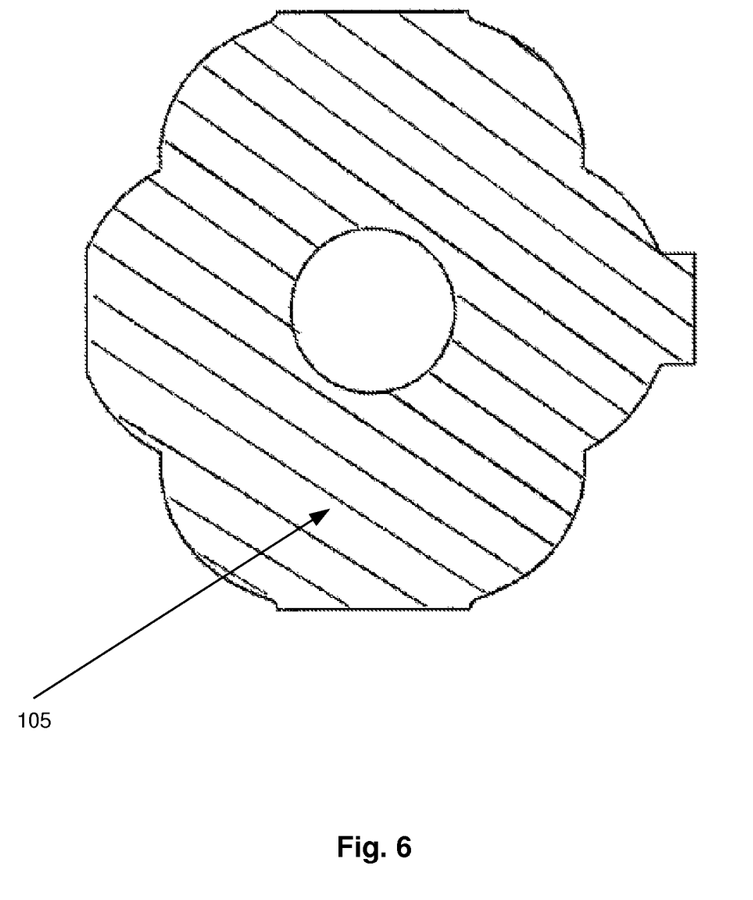
FIG. 6 is a side view from of the proximal side of a device according to one embodiment of the present invention, during a specific state.

In this way, a user or applier may (i) position the device 100 over the stoma of the patient, after the third covering sheet has been removed, by holding on the first and second covering sheets 110, 111; squeezing the device 100 in the medially, without deforming the tubular part 102 too much, due to the bracing means 107, and safely apply the device with good skin contact, even on sunken stomas, due to the convexly shaped proximal side of the flange 102, whereby the application of the device 100 is facilitated by only having the central/medial segment 112 skin-adhesive during application; thereafter (ii) pull the flaps 116, 117 laterally and thus uncovering, in a lateral direction, the skin-adhesive parts of the flange 102 covered by the first and second covering sheets 110, 111, until the first and second covering sheets 110, 111 has been removed and detached from the device 100, whereby the entire skin adhesive proximal side 105 of the device is exposed, as disclosed in the side view from the proximal side of the device according to FIG. 6, and then (iii) press the flange 102 towards the patient to assure satisfactory adhesion between the flange 102 and the skin of the patient.

Although the present invention has been described above with reference to specific embodiments, it is not intended to be limited to the specific form set forth herein. Rather, the invention is limited only by the accompanying claims and, other embodiments than the specific above are equally possible within the scope of these appended claims.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A device for holding a tracheostoma device over a tracheostoma of a patient comprising: a tubular portion defining a passage having a distal and a proximal opening, the tubular portion being configured to receive the tracheostoma device at the distal opening thereof and hold the tracheostoma device over the tracheostoma;
a flange extending radially from and about a circumference of said tubular portion, said flange forming a conical shape that is inclined proximally towards a central axis of said passage, said flange having a proximal side configured to face the tracheostoma of the patient, and a distal side configured to face outwardly from the patient, at least a part of said proximal side comprising a skin adhesive,
said flange having a higher moment of resistance in a lower/upper direction from said tubular portion than in a transverse direction from said tubular portion by having a higher moment of resistance in the lower/upper direction than in the transverse direction for at least a part of said flange;
wherein said higher moment of resistance in the lower/upper direction is obtained by a plurality of reinforcements on the distal side of the flange and extending from the circumference of said tubular portion, such that at least one of the reinforcements extends tangentially and in a lower direction from said tubular portion and at least another one of the reinforcements extends tangentially and in an upper direction from said tubular portion, so as to provide the device with an improved resistance to flipping over in the lower/upper direction.

2. The device according to claim 1, wherein each one of said reinforcements is a bracing mechanism on said flange, extending in one of the upper and lower directions from said tubular portion.

3. The device according to claim 2, wherein said bracing mechanism is a plurality of ribs.

4. The device according to claim 2, wherein said bracing mechanism has a higher material thickness in the lower/upper direction than in the transverse direction.

5. The device according to claim 1, wherein at least one weakening line is arranged in the lower/upper direction, giving a higher moment of resistance in the lower/upper direction than in the transverse direction for said device by having a higher moment of resistance in the lower/upper direction than in the transverse direction for at least a part of said flange, said at least one weakening line increasing the moment of resistance in the lower/upper direction relative to the transverse direction.

6. The device according to claim 1, wherein said flange extends from said tubular portion at a proximal part of said passage.

7. The device according to any claim 1, wherein said flange comprises an inner rigid portion extending radially from and about the circumference of said tubular portion and an outer more flexible portion extending radially from and about a periphery of the inner rigid portion.

8. The device according to claim 7, wherein each one of said reinforcements is positioned on said inner rigid portion.

9. The device according to claim 7, wherein a weld is located radially from said tubular portion, said weld connecting said inner rigid portion with said outer more flexible portion at a periphery of said inner rigid portion.

10. The device according to claim 1, wherein said flange includes a substantially circular or oval periphery forming the conical shape.

11. The device according to claim 1, wherein said flange includes an inner rigid portion that is inclined proximally towards said central axis of said passage.

12. The device according to claim 11, wherein said inner rigid portion is substantially oval, having an approximated longest diameter in the lower/upper direction and an approximated shortest diameter in the transverse direction.

13. The device according to claim 1, wherein each of a first, second, and third covering sheet is applied to said proximal side of said flange, said first and second covering sheets being applied laterally on each side of said passage, respectively, and said third covering sheet being applied centrally and medially and extending in lower and upper directions from said tubular portion.

14. The device according to claim 13, wherein the first and second covering sheets are folded laterally, and extend at least partly beyond a periphery of said flange.

15. The device according to claim 14, wherein each of the folded parts of said first and second covering sheets comprises a gripping flap, each extending beyond the periphery of said flange.

16. The device according to claim 1, wherein said device is a device for holding at least one of a heat moisture exchange device and speech valve.

17. The device according to claim 1, wherein the plurality of reinforcements on the flange includes two reinforcements extending in the lower direction from said tubular portion and two reinforcements extending in the upper direction from said tubular portion.

18. A method for applying a device over a stoma of a patient, comprising the steps of:

removing at least a third covering sheet that extends in lower and upper directions from a tubular portion of the device, thereby exposing a first covering sheet and a second covering sheet, the tubular portion defining a passage having a distal and a proximal opening, the tubular portion being configured to receive a tracheostoma device at the distal opening thereof;

positioning the device over the stoma of the patient;

removing the first and second covering sheets exposing a skin adhesive on a proximal side of a flange of the device that extends from and about a circumference of the tubular portion, said flange forming a conical shape that is inclined proximally towards a central axis of said passage, said flange further comprising a distal side configured to face outwardly from the patient;

adhering the skin adhesive on the proximal side of the flange of the device to at least a portion of skin on a neck of the patient; and providing a plurality of reinforcements on the distal side of the flange so as to provide a higher moment of resistance in a lower/upper direction from said tubular portion, such that at least one of the reinforcements extends tangentially and in a lower direction from said tubular portion and at least another one of the reinforcements extends tangentially and in an upper direction from said tubular portion, such that the device has an improved resistance to flipping over in the lower/upper direction.

19. A device for holding a tracheostoma device over a tracheostoma of a patient comprising:

a tubular portion defining a passage having a distal and a proximal opening, the tubular portion being configured to receive the tracheostoma device at the distal opening thereof;

a flange extending radially from and about a circumference of said tubular portion, said flange having a proximal side configured to face the tracheostoma of the patient and a distal side configured to face outwardly from the patient, said flange forming a conical shape that is inclined proximally towards a central axis of said passage; and a plurality of reinforcements on the distal side of the flange and configured to provide the flange with a higher moment of resistance in a lower/upper direction than in a transverse direction, at least one of the reinforcements extending tangentially and in a lower direction from said tubular portion and at least another one of the reinforcements extending tangentially and in an upper direction from said tubular portion, thereby providing an improved resistance to flipping over in the lower/upper direction.

* * * * *